United States Patent
Braddock, Jr. et al.

(10) Patent No.: US 7,621,953 B2
(45) Date of Patent: Nov. 24, 2009

(54) END DEVICE FOR A VERTEBRAL IMPLANT

(75) Inventors: Danny Horton Braddock, Jr., Germantown, TN (US); Dean G. Karahalios, Lake Forest, IL (US)

(73) Assignee: Warsaw Orthopedic, Inc.

( * ) Notice: Subject to any disclaimer, the term of this patent is extended or adjusted under 35 U.S.C. 154(b) by 209 days.

(21) Appl. No.: 11/434,051

(22) Filed: May 15, 2006

(65) Prior Publication Data

US 2007/0129805 A1  Jun. 7, 2007

Related U.S. Application Data

(63) Continuation-in-part of application No. 11/291,419, filed on Dec. 1, 2005.

(51) Int. Cl.
*A61F 2/44* (2006.01)

(52) U.S. Cl. .................................. 623/17.11

(58) Field of Classification Search ... 623/17.11–17.16; 606/61
See application file for complete search history.

(56) References Cited

U.S. PATENT DOCUMENTS

| | | | | |
|---|---|---|---|---|
| 3,210,820 | A | * | 10/1965 | Humiston ............ 24/704.1 |
| 3,502,396 | A | * | 3/1970 | Greenberg et al. ........ 351/157 |
| 4,401,112 | A | | 8/1983 | Rezaian |
| 4,657,550 | A | | 4/1987 | Daher |
| 4,820,305 | A | | 4/1989 | Harms et al. |
| 4,932,975 | A | | 6/1990 | Main et al. |
| 5,026,373 | A | | 6/1991 | Ray et al. |
| 5,062,850 | A | | 11/1991 | MacMillian et al. |
| 5,236,460 | A | * | 8/1993 | Barber .................. 623/17.15 |
| 5,336,223 | A | | 8/1994 | Rogers |
| 5,571,190 | A | * | 11/1996 | Ulrich et al. ............ 623/17.11 |
| 5,571,192 | A | | 11/1996 | Schonhoffer |
| 5,702,451 | A | * | 12/1997 | Biedermann et al. ...... 623/17.16 |
| 5,702,453 | A | | 12/1997 | Rabbe et al. |
| 5,702,455 | A | | 12/1997 | Saggar |
| 5,776,197 | A | | 7/1998 | Rabbe et al. |
| 5,989,290 | A | | 11/1999 | Biedermann et al. |
| 6,086,613 | A | | 7/2000 | Camino et al. |
| 6,190,413 | B1 | | 2/2001 | Sutcliffe |
| 6,193,755 | B1 | | 2/2001 | Metz-Stavenhagen et al. |
| 6,193,756 | B1 | * | 2/2001 | Studer et al. ............ 623/17.15 |
| 6,296,665 | B1 | | 10/2001 | Strnad et al. |

(Continued)

FOREIGN PATENT DOCUMENTS

DE  195 09 317 A1  9/1996

(Continued)

*Primary Examiner*—Thomas C Barrett
*Assistant Examiner*—Nicholas Woodall

(57) ABSTRACT

The present application is directed to spacing devices that attach directly or indirectly to vertebral implants. The spacing device may include a first side that faces the implant, and an angled second side that faces towards a vertebral member. The angled second side matches the shape of the vertebral member. The devices may further include apertures that receive spikes that extend outward from the implant. The second side may also include spikes that bite into and maintain the position of the device against the vertebral member. In one method of use, the spacing device may be rotated relative to the implant for the angled second side to match the vertebral member. The apertures are then placed over the spikes that extend outward from the implant to connect the spacing device to the implant.

15 Claims, 7 Drawing Sheets

U.S. PATENT DOCUMENTS

| | | |
|---|---|---|
| 6,344,057 B1 | 2/2002 | Rabbe et al. |
| 6,375,681 B1 | 4/2002 | Truscott |
| 6,375,683 B1 | 4/2002 | Crozet et al. |
| 6,395,034 B1 | 5/2002 | Suddaby |
| 6,520,991 B2 | 2/2003 | Huene |
| 6,616,695 B1 | 9/2003 | Crozet et al. |
| 6,645,249 B2 | 11/2003 | Ralph et al. |
| 6,660,038 B2 | 12/2003 | Boyer, II et al. |
| 6,719,796 B2 | 4/2004 | Cohen et al. |
| 6,758,862 B2 | 7/2004 | Berry et al. |
| 6,776,798 B2 | 8/2004 | Camino et al. |
| 6,808,538 B2 * | 10/2004 | Paponneau ............... 623/17.16 |
| 6,899,734 B2 | 5/2005 | Castro et al. |
| 6,908,485 B2 | 6/2005 | Crozet et al. |
| 6,929,662 B1 | 8/2005 | Messerli et al. |
| 6,991,653 B2 * | 1/2006 | White et al. ............. 623/17.16 |
| 7,238,205 B2 * | 7/2007 | Karahalios ............... 623/17.11 |
| 2004/0181283 A1 | 9/2004 | Boyer et al. |
| 2004/0186569 A1 | 9/2004 | Berry |
| 2005/0004572 A1 | 1/2005 | Biedermann et al. |
| 2006/0058879 A1 * | 3/2006 | Metz-Stavenhagen .... 623/17.15 |

FOREIGN PATENT DOCUMENTS

| | | |
|---|---|---|
| FR | 2 636 227 | 3/1990 |

* cited by examiner

_US 7,621,953 B2_

END DEVICE FOR A VERTEBRAL IMPLANT

RELATED APPLICATION

The present application is a continuation-in-part of U.S. patent application Ser. No. 11/291,419 filed Dec. 1, 2005.

BACKGROUND

Various procedures include removing the entirety or a section of a vertebral member. The procedures may also include removing more than one section or entirety of vertebral members. These procedures may be required due to damage to the vertebral member, such as that caused by a specific event such as trauma, a degenerative condition, a tumor, or infection.

Once the vertebral member is removed, an implant is inserted to replace the removed member or members. The implant maintains the spacing of the remaining vertebral members providing for them to function properly. The positioning and size of the implant are carefully determined prior to insertion. Once inserted, the implant should remain in position.

One surgical concern is securely interposing a vertebral implant between the remaining vertebral members to ensure that the implant can resist axial, torsional, and shear loading without causing anterior displacement ("kick-out"), posterior retropulsion of the implant and any associated graft material, or subsidence. Existing vertebral implants which attempt to minimize these methods of failure can often result in other undesirable consequences such as instrumentation pull-out, graft dislodgment, or erosion of nearby vascular and soft tissue structures due to high profile design.

SUMMARY

The present application is directed to spacing devices that attach directly or indirectly to vertebral implants. The spacing devices may include a first side that faces the implant, and an angled second side that faces towards a vertebral member. The angled second side matches the shape of the vertebral member. The devices may further include apertures sized to receive spikes that extend outward from the implant. The second side may also include spikes that bite into and maintain the position of the device against the vertebral member. In one method of use, the spacing device may be rotated relative to the implant for the angled second side to match the vertebral member. The apertures are then placed over the spikes that extend outward from the implant to connect the spacing device to the implant.

DETAILED DESCRIPTION

Figure 1:
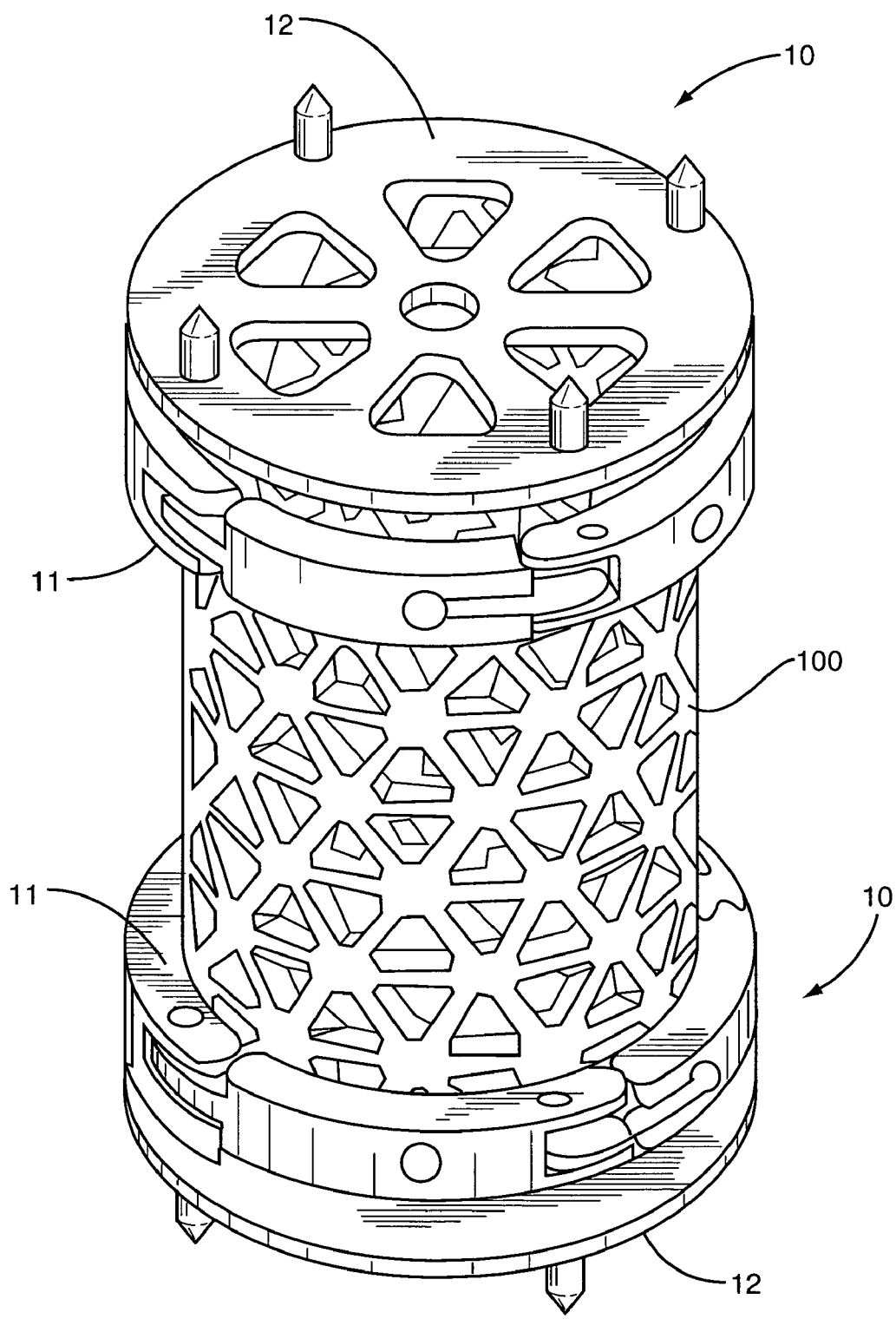
FIG. 1 is a perspective view of a pair of end devices mounted to an implant according to one embodiment.

FIG. 1 illustrates a pair of end devices, generally illustrated as element 10, each attached to one end of a vertebral implant 100. The end device 10 includes a first side 11 that faces towards the implant 100, and a second side 12 that faces towards a vertebral member. A receiving mechanism within the end device 10 is selectively positionable between open and closed orientations. The open orientation provides for inserting the implant 100 within a receiving area of the end device 10. The closed orientation prevents the implant 100 from being removed from the receiving area of the end device 10.

The term "implant" is used generally herein to describe a device that is inserted into a patient. Implant 100 may be inserted into a patient for a variety of purposes, and may have a variety of shapes and sizes. In the embodiment of FIG. 1, implant 100 has a cylindrical shape with a hollow interior for holding bone-growth material. One example of such a cylinder is disclosed in U.S. Pat. Nos. 5,897,556 and 6,149,651, which are incorporated herein by reference. The cylindrical body may comprise angled, intersecting elongate bars which form a plurality of triangular apertures. The cylindrical body defines a hollow bore configured to receive bone growth material.

Figure 2:
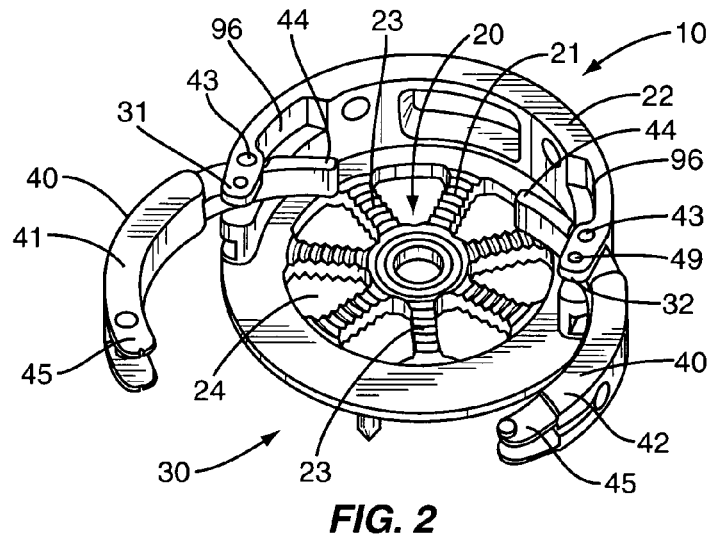
FIG. 2 is a perspective view of an end device in an open orientation according to one embodiment.
Figure 3:
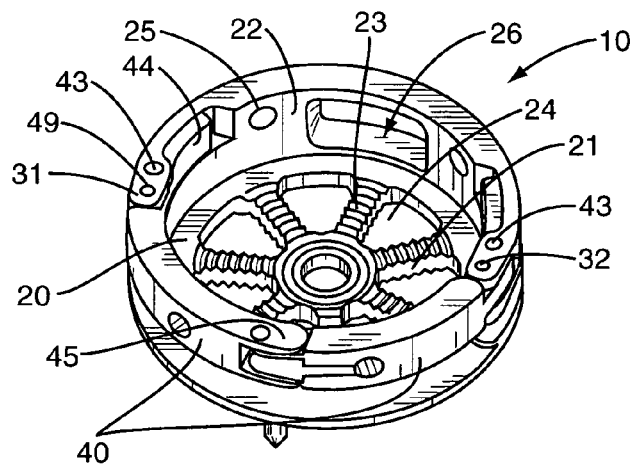
FIG. 3 is a perspective view of an end device in a closed orientation according to one embodiment.

FIGS. 2 and 3 illustrate the end device 10 with FIG. 2 illustrating an open orientation and FIG. 3 a closed orientation. An end device 10 is connected to the implant 100 and prevents subsidence, expulsion, and/or enables fusion. An implant 100 may be equipped with a single or multiple end devices 10. For implants 100 equipped with multiple end devices 10, the devices may be the same or different. In the embodiments of FIGS. 2 and 3, end device 10 includes a base 20, opening 30, and a gate 40. Base 20 includes a bottom 21 and a sidewall 22. A receiving area 26 is framed by the base 20 and gate 40 to receive the implant 100.

Bottom 21 shields the end members of the implant 100 from contacting the vertebral member. Bottom 21 may be constructed of supports 23 spaced apart with gaps 24 for bone growth material in the implant 100 to reach the vertebral member for bone and tissue ingrowth and vascularization. Supports 23 and gaps 24 may have a variety of shapes and sizes. The bottom 21 may further have a roughened surface to connect with the implant 100, such as when the implant 100 comprises a bone strut. Sidewalls 22 extend outward from the bottom 21 forming the receiving area 26. Sidewalls 22 may extend a variety of heights from the bottom 21 depending upon the context. Apertures 25 may extend through the sidewalls 22 and may be threaded to receive a fastener that connects the end device 10 to the implant 100. Apertures 25 also provide for the bone growth material to reach the vertebral member.

Figure 4:
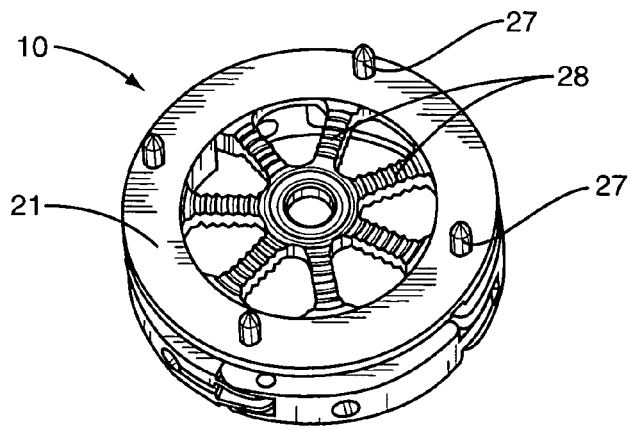
FIG. 4 is a perspective view of a second side of the end device according to one embodiment.

The outer surface of the bottom 21 is constructed to maintain the position relative to the vertebral member. As illustrated in FIG. 4, spikes 27 having a sharp tip may be positioned at spaced intervals to bite into the vertebral member. Ridges 28 may also be positioned along the surface to maintain the device position. The outer surface may also be roughened such as by a grit blast to further maintain the device position.

Opening 30 is positioned within the sidewall 22 and sized for the insertion of the implant 100. Opening 30 is defined between a first edge 31 and a second edge 32.

Gate 40 is selectively positionable between open and closed orientations for positioning and containing the implant 100 within the receiving area 26. Gate 40 comprises first member 41 and second member 42. Each of the members 41, 42 is movably connected to the sidewall 22 at a pivot 43. This connection provides for movement between the open orientation as illustrated in FIG. 2, and the closed orientation as illustrated in FIG. 3. Each member 41, 42 has an elongated shape having a first end 44 and a second end 45. Pivot 43 is positioned at a point intermediate between the ends 44, 45. In the open orientation, the first ends 44 are positioned within the receiving area 26 defined within the sidewalls 22. In the open orientation, a distance between the first ends 44 is less than a distance between the edges 31, 32. In the open orientation, the second ends 45 are spaced away from the opening 30 with a distance between the second ends 45 being greater than the distance between the edges 31, 32. The extent of pivoting may vary depending upon the application. In one embodiment, the gates 40 have a swing of about 50° between the open and closed orientations.

Members 41, 42 have an arcuate shape that matches the sidewalls 22 and extends around the periphery of the bottom 21 when in the closed orientation. In the embodiment of FIG. 3, members 41, 42 have a length for the ends 45 to be in an overlapping configuration when in the closed orientation. One or both ends 45 may include a lock mechanism to maintain the members 41, 42 in the closed orientation. In the embodiment of FIGS. 2 and 3, the lock mechanism includes a ball and detent combination that mates together in the closed orientation. First and second edges 31, 32 of the sidewalls may further include a locking mechanism that engages the members 41, 42. In one embodiment, each edge 31, 32 includes an indent or aperture 49 that receives a mating tab located on the members 41, 42 to further secure the members 41, 42 in the closed orientation. A deformable spring interface and a fastener may also be used to keep the gate in the closed orientation.

Figure 5:
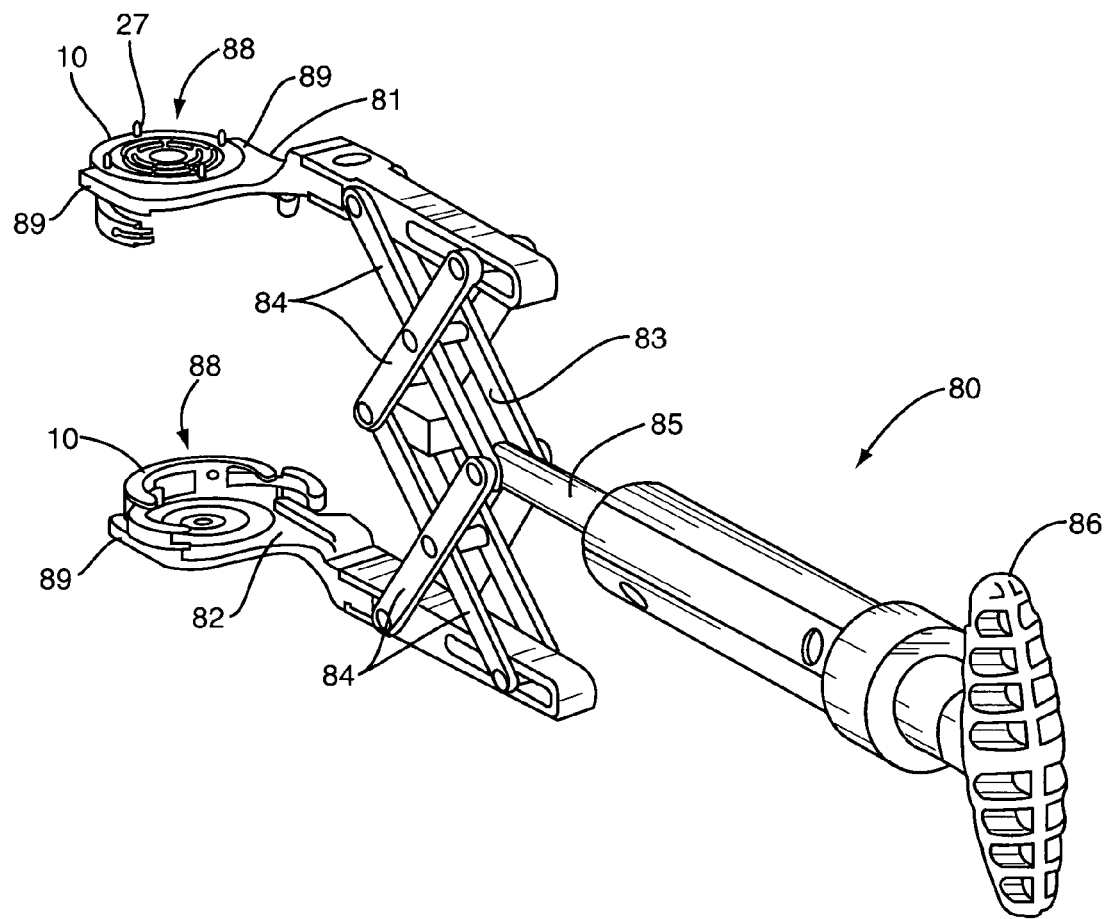
FIG. 5 is a perspective view of a pair of end devices mounted to an insertion device according to one embodiment.

Members 41, 42 may have the same or different height relative to the sidewalls 22. In the embodiments of FIGS. 2 and 3, members 41, 42 have a smaller height and are spaced upward from the bottom 21 with an upper edge of the members 41, 42 substantially matching an upper edge of the sidewalls 22. This gap between the members 41, 42 and the bottom 21 forms a space for the insertion device 80 as illustrated in FIG. 5.

Insertion device 80 is constructed to position the devices 10 relative to the vertebral members. Device 80 includes first and second arms 81, 82 each sized to hold an end device 10. Each arm 81, 82 has spaced-apart fingers 89 forming a capture area to receive the end devices 10. The fingers 89 form an opening 88 sized to slide the end devices 10 into the capture area. An adjustment mechanism 83 controls the distance between the arms 81, 82. In this embodiment, adjustment mechanism 83 is a jack device having pivoting linkages 84 attached to an arm 85. Handle 86 is operatively connected to the arm 85 to control the movement of the linkages 84 and thus the relative spacing of the arms 81, 82.

In use, one or two end devices 10 are slid through the openings 88 formed by the fingers 89 on the arms 81, 82. The end devices 10 are positioned in the capture area defined by the arms 81, 82 with the spikes 27 extending outward in preparation for positioning within the vertebral members. Further, the gates 40 are in the open orientation.

With the end devices 10 attached, the arms 81, 82 are positioned in a relatively closed orientation and are spaced apart a distance to fit between the remaining vertebral members. The surgeon then manipulates the handle 86 to insert the arms 81, 82 with the end devices 10 between the vertebral members. Once inserted, handle 86 is rotated to move apart the arms 81, 82. This movement causes the spikes 27 to be driven into the vertebral members to attach the end devices 10. The expansion movement may also distract the vertebral members.

With the end devices 10 in the open orientation, the implant 100 is moved through the gates 40 and into the receiving area 26. The gates 40 in the open orientation retract the soft tissue that may surround the vertebral members and keep open the line of sight for the surgeon. Once the end devices 10 are inserted, the implant 100 is inserted through the opening 30 and contacts the first ends 44 of the arms 41, 42. Further insertion of the implant 100 into the receiving area 26 causes the arms 41, 42 to move about their respective pivots 43 towards the closed orientation. In one embodiment, complete insertion of the implant 100 into the receiving area 26 results in the arms 41, 42 becoming locked together. In another embodiment, the surgeon locks the arms 41, 42 together after the insertion of the implant 100.

Once the implant 100 and end devices 10 are inserted, the insertion device 80 is removed from the end devices 10. The opening 88 in the arms 81, 82 is aligned facing away from the handle 86. The surgeon manipulates the handle 86 and pulls the insertion device 80 in a proximal direction thus causing the end devices 10 and implant to slide out of the fingers 89 and remain between the vertebral members.

The embodiments illustrated in FIGS. 2 and 3 include a gate 40 having first and second members 41, 42. Gate 40 may further comprise a single member that extends across the opening 30 to prevent escape of the implant 100. Both the single gate and multiple gate embodiments may extend across the entirety or a portion of the opening 30. The embodiment of FIGS. 2 and 3 illustrate the first and second members 41, 42 extending across the entirety of the opening 30. Other embodiments include the gate 40 being smaller than the opening leaving a gap that is of a smaller size than the implant 100 thus preventing escape.

Figure 6:
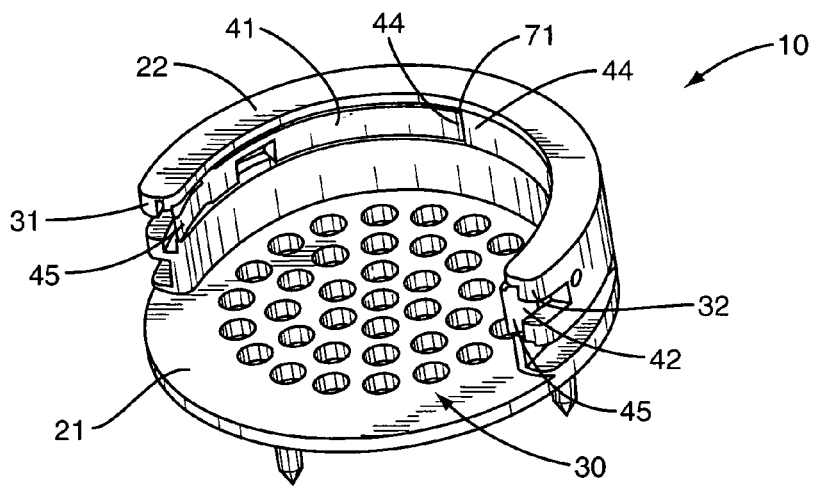
FIG. 6 is a perspective view of an end device having a sliding gate in an open orientation according to one embodiment.
Figure 7:
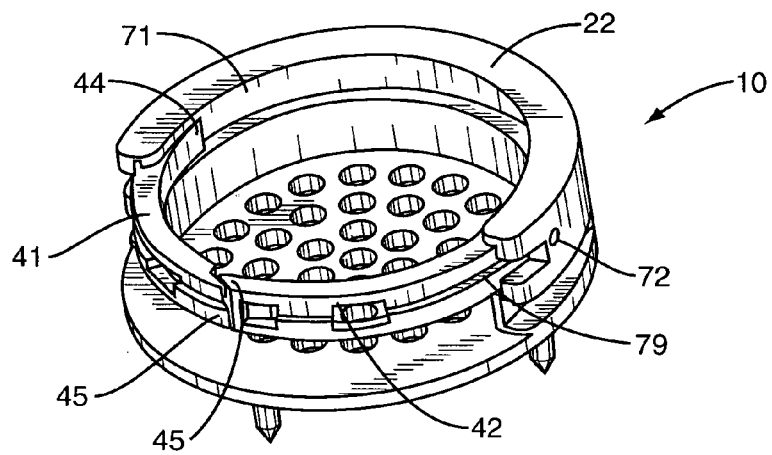
FIG. 7 is a perspective view of an end device having a sliding gate in a closed orientation according to one embodiment.

Another embodiment of a gate 40 features a sliding attachment with the base 20. As illustrated in FIGS. 6 and 7, sidewalls 22 include a slot 71 within an inner face. First and second members 41, 42 are sized to slide within the slot between an open orientation as illustrated in FIG. 6, and a closed orientation as illustrated in FIG. 7. Slot 71 may extend around the entirety of the sidewall 22, or a limited section adequate to receive the members 41, 42 an amount to clear the opening 30 for insertion of the implant 100. In the embodiment of FIG. 6, the first ends 44 of the members 41, 42 make contact in the open orientation with the second ends 45 being within the sidewalls 22. In the closed orientation, second ends 45 are in contact. Members 41, 42 may be attached within the sidewall 22 to prevent full removal. In one embodiment as illustrated in FIG. 7, pins 72 within the sidewall 22 are positioned within a groove 79 in the members 41, 42 to prevent the complete removal.

In other embodiments of this sliding arrangement, first ends 44 may be spaced apart in the open orientation, and second ends 45 may not be in contact in the closed orientation. In another embodiment, multiple members may be used, as opposed to the single member configuration illustrated in FIGS. 6 and 7. In another embodiment, slot 71 for receiving the members 41, 42 is positioned on an outer face of the sidewall 22.

Figure 8:
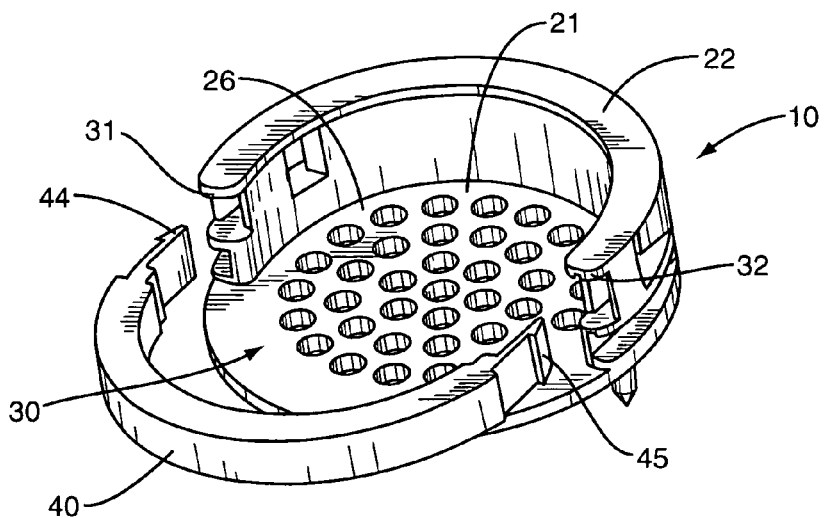
FIG. 8 is a perspective view of a removable gate according to one embodiment.

FIG. 8 illustrates another embodiment having a removable gate 40. Gate 40 includes first and second ends 44, 45 each having a locking mechanism that engages first and second edges 31, 32 of the sidewall 22. In the open orientation, gate 40 is removed allowing for the implant to be inserted through the opening 30 into the receiving area 26. In the closed orientation, gate 40 is mounted to the sidewalls 22 thereby enclosing the receiving area 26 and preventing escape of the implant 100. In another embodiment (not illustrated), the removable gate 40 is comprises of two or more sections. Each of the sections is separately removable from and attachable to the sidewalls.

In embodiments having a pivoting gate as illustrated in FIGS. 2 and 3, pivot 43 may be positioned at a variety of locations along the gate. In the embodiments of FIGS. 2 and 3, pivot 43 is positioned between the first and second ends 44, 45. In another embodiment, pivot 43 is positioned at the first end 45.

End device 10 may further include a combination of different gate configurations. By way of example, one section of the gate 40 may have a pivoting configuration, with a second section having a sliding or removable configuration. In one embodiment, gate 40 is configured for both sliding and pivoting.

In one embodiment of a pivoting gate as illustrated in FIGS. 2 and 3, one or both members 41, 42 have a tapered width that increases from the first end 44 towards the second end 45. Sidewall 22 includes a cutout section 96 into which the first end 44 is inserted when the gate 40 moves to the closed orientation. Cutout section 96 has a constant width. A section of the width of the members 41, 42 is slightly greater than the width of the cutout section 96. This causes the members 41, 42 to become slightly wedged into the cutout section 96 in the open orientation to maintain the members 41, 42 in the open orientation. The differences in widths between the cutout section 96 and the members 41, 42 is only slight thus not greatly increasing the amount of force required to move the move the members 41, 42 to the closed orientation. In another embodiment, the width of the members 41, 42 is constant and the cutout section 96 has a tapering width. In another embodiment, a ball detent mechanism is used to maintain one or both members 41, 42 in the open orientation.

A spacing device 101 may be positioned on a second side 12 of the end device 10. The spacing device 101 may have an angled shape such that the end device 10 with implant 100 corresponds to the curvature of the spine. The spacing device 101 may be separately attached to the bottom surface, or may be integral with the bottom surface.

Figure 9:
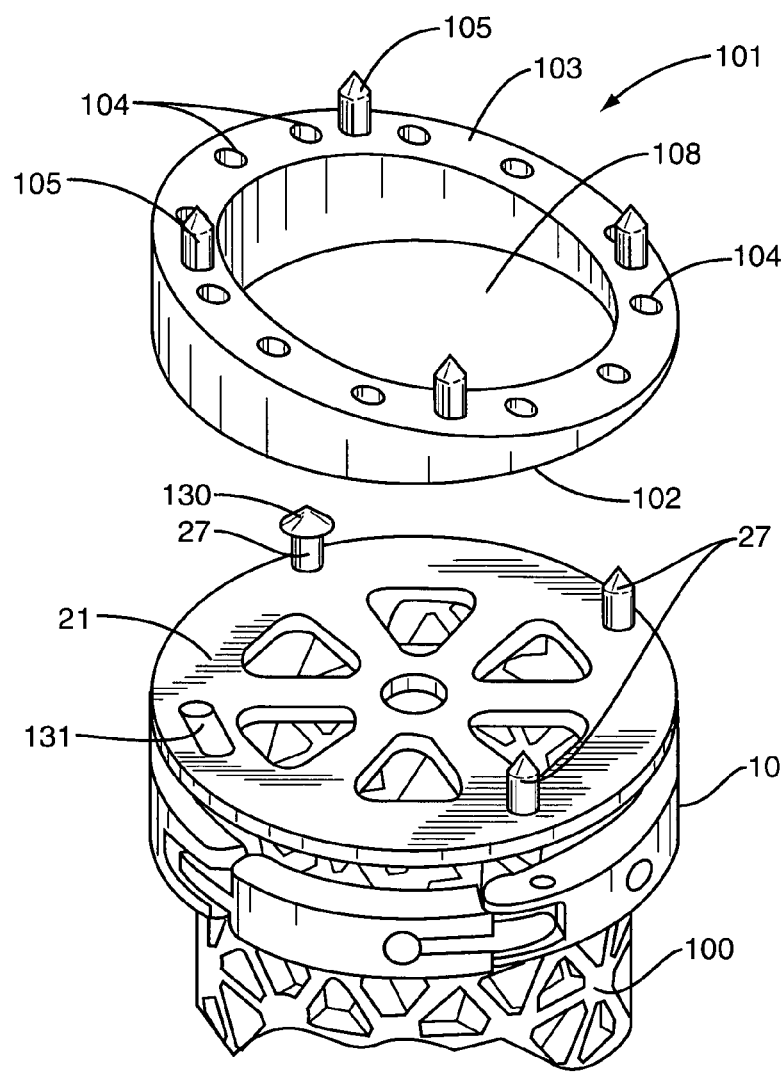
FIG. 9 is an exploded perspective view of a spacing device and an end device according to one embodiment.

FIG. 9 illustrates one embodiment of the spacing device 101 with a first side 102 and an opposing second side 103. Apertures 104 are spaced about the device 101 and are sized to receive the spikes 27 that extend outward from the end device 10 to connect the spacing device 101 to the end device 10. Spikes 105 extend outward from the second side 103 to bite into the vertebral member and prevent movement or expulsion of the device 101.

Figure 10:
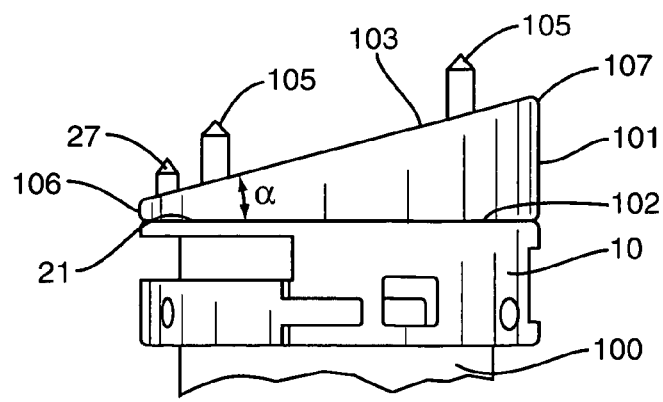
FIG. 10 is a side view of a spacing device seated against an end device according to one embodiment.
Figure 12:
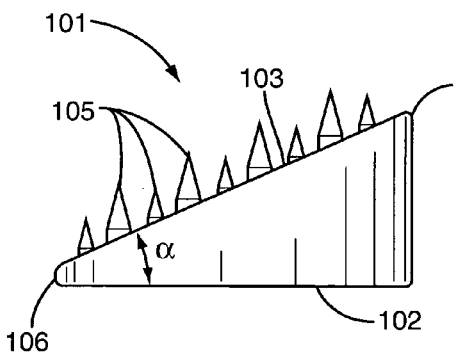
FIG. 12 is a side view illustrating a spacing device according to one embodiment.
Figure 13:
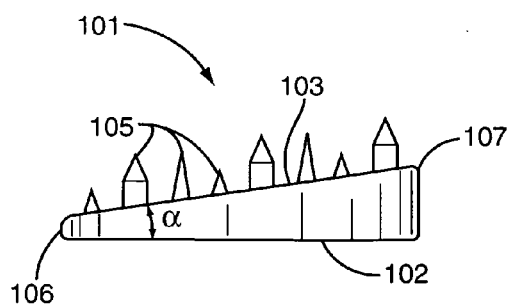
FIG. 13 is a side view illustrating a spacing device according to one embodiment.

The first side 102 may be substantially flat to contact against the bottom 21 of the end device 10. As illustrated in FIG. 10, the flat shape provides for a large contact area with the bottom 21. The second side 103 is positioned at an angle α relative to the first side 102. The amount of angle may vary to match the shape of vertebral member. FIG. 12 illustrates an embodiment with a greater angle α than a second embodiment illustrated in FIG. 13 with a smaller angle α. Sidewalls extend between the first and second sides 102, 103 with a first lateral edge 106 being smaller than a second lateral edge 107.

Apertures 104 are spaced about the device 101 to receive the spikes 27 that extend outward from the end device 10. The apertures 104 receive the spikes 27 for the device 101 to seat onto the end device 10 with the first side 102 contacting the bottom 21. The number of apertures 104 may be equal to or greater than the number of spikes 27.

Figure 14:
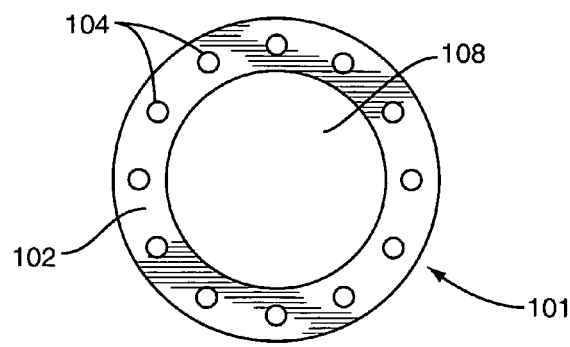
FIG. 14 is a bottom view illustrating a spacing device according to one embodiment.

The apertures 104 are spaced about the implant 101 to provide for selectively positioning the implant 101 onto the end device 10. In one embodiment with four apertures 104 that receive four spikes 27, the device 101 may be selectively positioned at 90° increments. This adjustability allows the device 101 to closely match the contour of the vertebral member. Increasing the number of additional apertures 104 provides for smaller rotational increments. Using the embodiment of FIG. 14 as an example for use with an end device 10 with four spikes 27, the twelve apertures 104 allow selective positioning at 30° increments.

Figure 11:
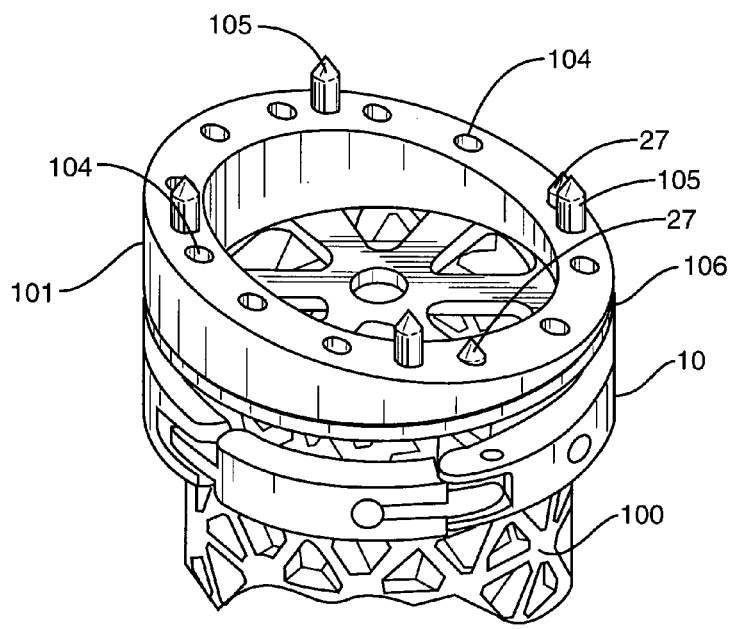
FIG. 11 is a perspective view of a spacing device seated against an end device according to one embodiment.

The apertures 104 may extend through the device 101 from the first side 102 to the second side 103. When the thickness of the device 101 is small, the spikes 27 may extend through the aperture and extend outward from the second side 103. FIGS. 10 and 11 illustrate embodiments with a spike 27 extending entirely through an aperture 104 and extending outward from the second side 103. In some embodiments, apertures 104 extend inward from the first side 102 but do not extend entirely through to the second side 103. In some embodiments, one or more of the apertures 104 extend entirely through the device 101 with the remaining apertures 104 extending partially through the device 101.

Spikes 105 extend outward from the second side 103 to bite into the vertebral member. The spikes 105 may include a variety of shapes and sizes. The second side 103 may further include surface features such as these are used to promote bone growth and adhesion at the interface between a device 101 and vertebral member. Examples of features used for this purpose include, for example, teeth, scales, keels, knurls, and roughened surfaces.

Figure 15:
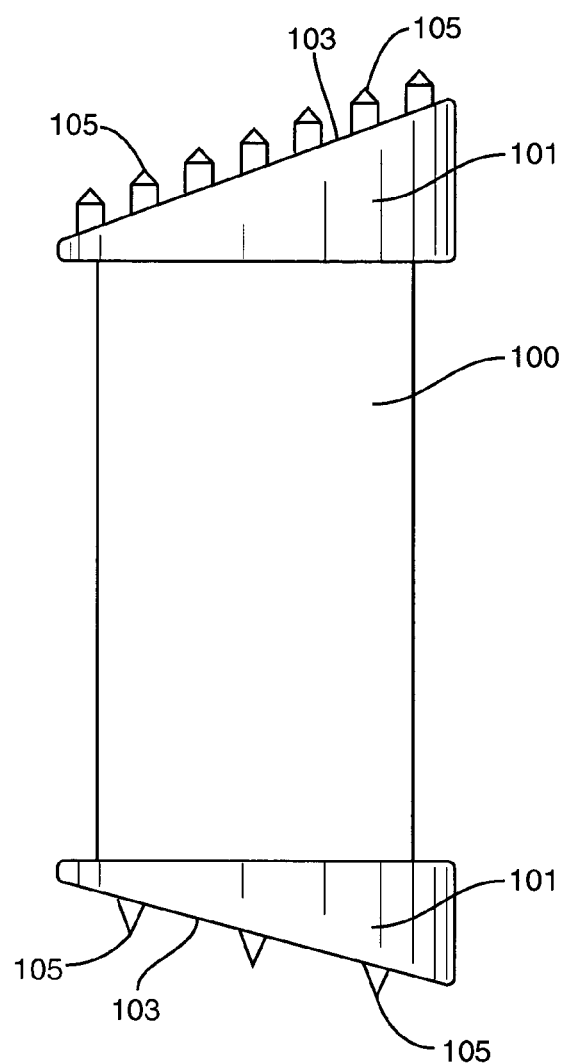
FIG. 15 is a side view illustrating a pair of spacing devices seated against an implant according to one embodiment.

The device 101 may be positioned on the outer surface of an end device 10 as illustrated in FIGS. 9-11. Device 101 may also be attached directly to an implant 100. FIG. 15 illustrates an embodiment with a pair of devices 101 positioned at the ends of the implant 100. The device 101 includes apertures 104 that mate with spikes 27 that extend outward from the ends of the implant 100. Spikes 105 extend outward from the second side 103 to engage the vertebral members and maintain the position of the devices 101 and implant 100. Examples of implants 100 that may be attached with the device 101 include SCEPTOR and XVBR implants each available from Medtronic Sofamor Danek of Memphis, Tenn., and herein incorporated by reference.

In one embodiment as illustrated in FIG. 10, the device 101 is approximately the same width as the end device 10 and the implant 100. In another embodiment as illustrated in FIG. 15, the device 101 includes a greater width than the implant 100.

Figure 16:
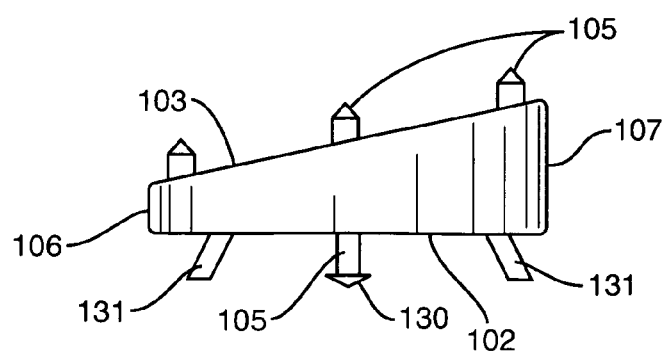
FIG. 16 is a side view illustrating a spacing device according to one embodiment.

The end device 101 may also includes spikes 105 that extend outward from the first side 102 as illustrated in FIG. 16. These spikes 105 mate with apertures 104 on the bottom 21 to attach the device 101. In some embodiment, each of the bottom 21 and the first side 102 include a combination of spikes 105 and apertures 104 that mate together.

The end device 101 may be attached to the end device 10 or implant 100 to prevent inadvertent removal. In one embodiment, one or more of the spikes 27 include a flared end 130 as illustrated in FIG. 9. The flared end 130 includes a larger width than the apertures 104. During insertion of the spike 27 into the aperture, the flared end 130 is deformed which applied an attachment force to maintain the attachment. One or more of the spikes 27 may include a flared end 130. Spikes 105 with flared ends 130 may also extend outward from the first side 102 as illustrated in FIG. 16 and mate with apertures on the device 10 or implant 100.

Deformable fingers 131 may further extend outward from the end device 10 or implant 100 to maintain attachment. Fingers 130 are sized to fit within the apertures 104 and are constructed of a deformable material. The fingers are bent or otherwise deformed during insertion into the aperture 104 to maintain attachment. In one specific embodiment, fingers 130 are coil springs. One or more deformable fingers 131 may provide attachment of the spacing device 101. Fingers 131 may also extend outward from the first side 102 and mate with apertures on the device 10 or implant 100.

The term "distal" is generally defined as in the direction of the patient, or away from a user of a device. Conversely, "proximal" generally means away from the patient, or toward the user. Spatially relative terms such as "under", "below", "lower", "over", "upper", and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc and are also not intended to be limiting.

The present invention may be carried out in other specific ways than those herein set forth without departing from the scope and essential characteristics of the invention. In one embodiment, bottom 21 of base 20 is solid. In another embodiment, the supports 23 are deleted, and the bottom 21 of the base 20 is open, with only a rim remaining to support the implant 100. In another embodiment, supports 23 are removable, and connect to the bottom 21 as a separate element intended to contain bone fusion material. The individual members 41, 42 may have the same or different sizes and shapes. In one embodiment, sidewall 22 is positioned inward from an outer edge of the bottom 21. The present embodiments are, therefore, to be considered in all respects as illustrative and not restrictive, and all changes coming within the meaning and equivalency range of the appended claims are intended to be embraced therein.

What is claimed is:

1. A device for spacing first and second vertebral members comprising:
    an implant including first and second opposing ends with implant spikes that extend outward from at least the first end and an implant aperture in the first end;
    a spacer configured to attach to the first end of the implant comprising:
        a first surface that faces towards the implant;
        a second surface configured to face towards the first vertebral member, the second surface being positioned at an acute angle relative to the first surface;
        a plurality of apertures that extend into the first surface and through to the second surface with each of the plurality of apertures sized to receive one of the implant spikes; and
        a plurality of spikes that extend outward from the second surface configured to engage the vertebral member; and
        an extension extending outward from the first surface and including a flared end sized to fit within the implant aperture in the first end;
    the spacer including a thickness measured between the first and second surfaces that is less than a length of at least one of the implant spikes for the implant spike to extend through the spacer and outward beyond the second surface to engage with the vertebral member.

2. The device of claim 1, wherein the first and second surfaces are substantially flat.

3. The device of claim 1, wherein the spacer further comprises a central opening that is surrounded by a sidewall.

4. The device of claim 1, wherein each of the plurality of apertures are evenly spaced around the second surface with a distance between each of the plurality of apertures being substantially the same.

5. The device of claim 1, further comprising an attachment member that extends outward from the first surface to attach with the implant.

6. A device for spacing first and second vertebral members comprising:
    an implant including first and second opposing ends, the first end including a receiving aperture;
    a spacer configured to attach to the first end of the implant comprising:
        an annular member including a first surface that faces towards the implant and a second surface configured to face towards the vertebral member, the second surface being positioned at an acute angle relative to the first surface;
        a plurality of apertures that extend into the first surface to receive implant spikes that extend outward from the implant, the plurality of apertures being evenly spaced around the first surface;
        a deformable finger that extends outward at a non-perpendicular angle from the first surface and is sized to fit within the receiving aperture in the first end of the implant;
        a plurality of spikes that extend outward from the second surface configured to engage the vertebral member; and
    an attachment member extending outward from the first surface, the attachment member including a flared end sized to fit within a second aperture in the first end of the implant to attach the annular member to the implant.

7. The device of claim 6, further comprising an attachment member extending outward from the first surface, the attachment member including a biasing member to attach the annular member to the implant.

8. The device of claim 6, wherein the first and second surfaces are substantially flat.

9. The device of claim 6, wherein the plurality of apertures extend through to the second surface.

10. The device of claim 9, wherein each of the plurality of apertures are evenly spaced around the second surface with a distance between each of the plurality of apertures being substantially the same.

11. A device for spacing first and second vertebral members comprising:

an implant including first and second opposing ends and an implant spike that extends outward from the first end;

a spacer configured to attach to the first end of the implant comprising:

a first surface that faces towards the implant;

a second surface configured to face towards the vertebral member, the second surface being positioned at an acute angle relative to the first surface;

a plurality of apertures that extend through the spacer from the first and second surfaces;

an attachment member that extends outward from the first surface to attach the spacer to the implant; and a plurality of spikes that extend outward from the second surface configured to engage the vertebral member;

the spacer including a first side with a first thickness measured between the first and second surfaces and a second side with a greater second thickness;

the implant spike including a length that is greater than the first thickness and less than the second thickness, an end of the implant spike extending outward beyond the second surface when mounted in one of the plurality of apertures adjacent to the first side and the implant spike positioned within an interior of the spacer between the first and second surfaces when mounted in one of the plurality of apertures at the second side.

12. The device of claim 11, wherein the attachment member includes a flared end.

13. The device of claim 11, further comprising a second attachment member extending outward from the first surface to attach the spacer to the implant.

14. The device of claim 11, wherein the plurality of apertures extend through to the second surface.

15. The device of claim 14, wherein each of the plurality of apertures are evenly spaced around the second surface with a distance between each of the plurality of apertures being substantially the same.

* * * * *

UNITED STATES PATENT AND TRADEMARK OFFICE
CERTIFICATE OF CORRECTION

PATENT NO. : 7,621,953 B2  Page 1 of 1
APPLICATION NO. : 11/434051
DATED : November 24, 2009
INVENTOR(S) : Braddock, Jr. et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 402 days.

Signed and Sealed this

Twenty-sixth Day of October, 2010

David J. Kappos
*Director of the United States Patent and Trademark Office*